(12) United States Patent
Gehlsen

(10) Patent No.: US 11,542,321 B2
(45) Date of Patent: Jan. 3, 2023

(54) ENGINEERED STABLE CH2 POLYPEPTIDES

(71) Applicant: RESEARCH CORPORATION TECHNOLOGIES, INC., Tucson, AZ (US)

(72) Inventor: Kurt R. Gehlsen, Tucson, AZ (US)

(73) Assignee: Research Corporation Technologies, Inc., Tucson, AZ (US)

( * ) Notice: Subject to any disclaimer, the term of this patent is extended or adjusted under 35 U.S.C. 154(b) by 425 days.

(21) Appl. No.: 16/495,245

(22) PCT Filed: Mar. 20, 2018

(86) PCT No.: PCT/US2018/023267
§ 371 (c)(1),
(2) Date: Sep. 18, 2019

(87) PCT Pub. No.: WO2018/175383
PCT Pub. Date: Sep. 27, 2018

(65) Prior Publication Data
US 2020/0031912 A1   Jan. 30, 2020

Related U.S. Application Data

(60) Provisional application No. 62/474,792, filed on Mar. 22, 2017.

(51) Int. Cl.
| | |
|---|---|
| C40B 40/10 | (2006.01) |
| C07K 16/18 | (2006.01) |
| C40B 30/04 | (2006.01) |
| C40B 20/04 | (2006.01) |

(52) U.S. Cl.
CPC .............. *C07K 16/18* (2013.01); *C40B 20/04* (2013.01); *C40B 30/04* (2013.01); *C40B 40/10* (2013.01); *C07K 2317/524* (2013.01); *C07K 2317/567* (2013.01)

(58) Field of Classification Search
None
See application file for complete search history.

(56) References Cited

U.S. PATENT DOCUMENTS

| | | |
|---|---|---|
| 7,842,476 B2 | 11/2010 | McGregor et al. |
| 8,557,744 B2 | 10/2013 | Coomber et al. |

(Continued)

FOREIGN PATENT DOCUMENTS

| | | |
|---|---|---|
| WO | 2009/099961 A2 | 8/2009 |
| WO | 2012/109553 A2 | 8/2012 |
| WO | 2013/119903 A1 | 8/2013 |
| WO | 2016/065258 A1 | 4/2016 |

OTHER PUBLICATIONS

Gehlsen K.R. et al., "Abstract 655: The Next Generation of Targeted Toxins: A Novel Deimmunized Sarcin Ribotoxin Fused With an EphA2 Abdurin Binder", vol. 75(15) (Aug. 1, 2015).

(Continued)

*Primary Examiner* — Christian C Boesen
(74) *Attorney, Agent, or Firm* — Scully, Scott, Murphy & Presser, P.C.

(57) ABSTRACT

This invention relates to engineered CH2 domain molecules containing amino acids in the framework regions that confer enhanced stability and/or solubility. In particular, the invention provides engineered CH2 domain molecules containing amino acid residues that differ from a wild type CH2 domain or a template CH2 domain molecule within one or more framework regions and that result in improved stability and/or solubility.

23 Claims, 4 Drawing Sheets
(3 of 4 Drawing Sheet(s) Filed in Color)

Specification includes a Sequence Listing.

| | Tm°C | FcRn binding (KD) | soluble expression |
|---|---|---|---|
| Human CH2 (SEQ ID NO: 1) | 56.6 | 12 nM | 900 ug/ml |
| Macaque CH2 (SEQ ID NO: 2) | 59.4 | 13 nM | 900 ug/ml |
| B11 (SEQ ID NO: 12) | 59.8 | 12 nM | 300 ug/ml |
| ABD01 (SEQ ID NO: 3) | 72.8 | 4.183 nM | 2386 ug/ml |
| ABD02 (SEQ ID NO: 4) | 66.2 | 21 nM | 785 ug/ml |
| ABD03 (SEQ ID NO: 5) | 70.4 | 11.45 nM | 1937 ug/ml |
| ABD04 (SEQ ID NO: 6) | 74.9 | 8.9 nM | 2112 ug/ml |
| ABD05 (SEQ ID NO: 7) | 72.5 | 9.1 nM | 1632 ug/ml |

(56) References Cited

U.S. PATENT DOCUMENTS

| | | |
|---|---|---|
| 8,679,781 B2 | 3/2014 | McGregor et al. |
| 2010/0316641 A1* | 12/2010 | Dimitrov ................ A61P 37/06 435/243 |
| 2016/0237130 A1 | 8/2016 | Stevis et al. |
| 2017/0037153 A1 | 2/2017 | Skolaut et al. |

OTHER PUBLICATIONS

Gehlsen K.R. et al., "Pharmacokinetics of Engineered Human Monomeric and Dimeric CH2 Domains", mAbs 4(4):466-474 (Jul./Aug. 2012).

Gong R. et al., "Shortened Engineered Human Antibody CH2 Domains: Increased Stability and Binding to the Human Neonatal Receptor", Journal of Biological Chemistry 286(31):1-14 (Aug. 5, 2011).

Gong R. et al., "Engineered Human Antibody Constant Domains With Increased Stability", The Journal of Biological Chemistry 284(21):14203-14210 (May 22, 2009).

Supplementary Partial European Search Report dated Dec. 11, 2020 received in European Patent Application No. 18 77 1174.2.

Dimitrov D.S., "Engineered CH2 Domain (Nanoantibodies)", mAbs 1(1):26-28 (Jan./Feb. 2009).

Odegrip R. et al., "CIS Display: In Vitro Selection of Peptides from Libraries of Protein-DNA Complexes", PNAS 101(9):2806-2810 (Mar. 2, 2004).

International Search Report dated Aug. 24, 2018 received in International Application No. PCT/US2018/023267.

\* cited by examiner

```
          10         20         30         40         50         60         70         80         90        100     SEQID
GPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK        1
GPSVFLFPPKPKDTLMISRTPEVTCVVVDVSQEDPDVKFNWYVNGAEVHHAQTKPRETQYNSTYRVVSVLTVTHQDWLNGKEYTCKVSNKALPAPIQKTISKDK        2

GPSVFLFPPKPKDTLMISRTPEVTCVVVDVSHEDPEVKFNWYVDGAEVHNAKTKPREEQYNSTYRVVSVLTVLHQDWLNGKEYTCKVSNKALPAPIEKTISKDK        22
GPSVFLFPPKPKDTLMISRTPEVTCVVVDVSHEDPEVKFNWYVDGAEVHHAKTKPREEQYNSTYRVVSVLTVLHQDWLNGKEYTCKVSNKALPAPIEKTISKDK        23
GPSVFLFPPKPKDTLMISRTPEVTCVFVDVSHEDPEVKFNWYVDGAEVHHAKTKPREEQYNSTYRVVSVLTVSHQDWLNGKEYTCKVSNKALPAPIEKTISKDK        24
GPSVFLFPPKPKDTMISRTPEVTCVFVDVSHEDPEVKFNWYVDGAEVHHAKTKPREEQYNSTYRVVSVLTVSHQDWLNGKEYTCKVSNKALPAPIQKTISKDK        25
GPSVFLFPPKPKDTLMISRTPEVTCVFVDVSHEDPEVKFNWYVDGAEVHHAKTKPREEQYNSTYRVVSVLTVSHQDWLNGKEYTCKVSNKALPAPIEKTISKDK        26

GPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK        12

GPSVFLFPPKPKDTLMISRTPEVTCVFVDVSHEDPEVKFNWYVDGAEVHNAKTKPRQYDPLYGYRVVSVLTVLHQDWLNGKEYTCKVSNKALPAPIEKTISKDK        3
GPSVFLFPPKPKDTLMISRTPEVTCVFVDVSHEDPEVKFNWYVDGAEVHHAKTKPRQYDPLYGYRVVSVLTVLHQDWLNGKEYTCKVSNKALPAPIEKTISKDK        4
GPSVFLFPPKPKDTLMISRTPEVTCVFVDVSHEDPEVKFNWYVDGAEVHHAKTKPRQYDPLYGYRVVSVLTVSHQDWLNGKEYTCKVSNKALPAPIEKTISKDK        5
GPSVFLFPPKPKDTMMISRTPEVTCVFVDVSHEDPEVKFNWYVDGAEVHHAKTKPRQYDPLYGYRVVSVLTVSHQDWLNGKEYTCKVSNKALPAPIQKTISKDK        6
GPSVFLFPPKPKDTLMISRTPEVTCVFVDVSHEDPEVKFNWYVDGAEVHHAKTKPRQYDPLYGYRVVSVLTVSHQDWLNGKEYTCKVSNKALPAPIEKTISKDK        7
```

| | Tm°C | FcRn binding (KD) | Soluble expression |
|---|---|---|---|
| Human CH2 (SEQ ID NO: 1) | 56.6 | 12 nM | 900 ug/ml |
| Macaque CH2 (SEQ ID NO: 2) | 59.4 | 13 nM | 900 ug/ml |
| B11 (SEQ ID NO: 12) | 59.8 | 12 nM | 300 ug/ml |
| ABD01 (SEQ ID NO: 3) | 72.8 | 4.183 nM | 2386 ug/ml |
| ABD02 (SEQ ID NO: 4) | 66.2 | 21 nM | 785 ug/Ml |
| ABD03 (SEQ ID NO: 5) | 70.4 | 11.45 nM | 1937 ug/ml |
| ABD04 (SEQ ID NO: 6) | 74.9 | 8.9 nM | 2112 ug/ml |
| ABD05 (SEQ ID NO: 7) | 72.5 | 9.1 nM | 1632 ug/ml |

FIGURE 4

ENGINEERED STABLE CH2 POLYPEPTIDES

CROSS REFERENCE TO RELATED APPLICATION

This application claims the benefit of priority of U.S. Provisional Application No. 62/474,792, filed Mar. 22, 2017, the entire contents of which is incorporated herein by reference.

FIELD OF THE DISCLOSURE

This invention relates to CH2 domain molecules containing amino acids in the framework regions that confer enhanced stability and/or solubility. In particular, the invention provides engineered CH2 domain molecules containing amino acid residues that differ from a wild type or a template CH2 domain molecule within one or more framework regions and that result in improved stability and/or solubility.

INCORPORATION BY REFERENCE TO SEQUENCE LISTING

The sequence listing in the ASCII text file, named as 34330 Sequence Listing.txt of 19 KB, created on Sep. 17, 2019, and submitted to the United States Patent and Trademark Office via EFS-Web, is incorporated herein by reference.

BACKGROUND ART

Immunoglobulins (antibodies) in adult humans are categorized into five different isotypes: IgA, IgD, IgE, IgG, and IgM. The heavy chains in IgG, IgA, and IgD each have a variable domain (VH) at one end followed by three constant domains: CH1, CH2, and CH3. The heavy chains in IgM and IgE each have a variable domain (VH) at one end followed by four constant domains: CH1, CH2, CH3, and CH4. Sequences of the variable domains vary, but the constant domains are generally conserved among all antibodies in the same isotype. The $F_{ab}$ region of immunoglobulins contains the variable (V) domain and the CH1 domain; the $F_c$ region of immunoglobulins contains the hinge region and the remaining constant domains, either CH2 and CH3 in IgG, IgA, and IgD, or CH2, CH3, and CH4 in IgM and IgE.

Target antigen specificity of the immunoglobulins is conferred by the paratope in the $F_{ab}$ region. Effector functions (e.g., complement activation, interaction with $F_c$ receptors such as pro-inflammatory $F_c\gamma$ receptors, binding to various immune cells such as phagocytes, lymphocytes, platelets, mast cells, and the like) of the immunoglobulins are conferred by the $F_c$ region. The $F_c$ region is also important for maintaining serum half-life. Serum (blood) half-life of an immunoglobulin is mediated by the binding of the $F_c$ region to the neonatal Fc receptor FcRn. The alpha domain is the portion of FcRn that interacts with the CH2 domain and CH3 domain interface of IgG, and possibly IgA, and IgD or with the CH3 domain and CH4 domain of IgM and IgE.

The CH2 domain (or the equivalent CH3 domain of IgM or IgE) also has binding sites for complement. The CH2/CH3 domain's retention of functional characteristics of the antibody from which it is derived (e.g., interaction with $F_c\gamma$ receptors, binding sites for complement, solubility, stability/half-life, etc.) is discussed in Dimitrov (2009) *mAbs* 1:1-3 and Dimitrov (2009) *mAbs* 1:26-28.

Isolated CH2 molecules (also referred to as "nanobodies") have been described in the art (Dimitrov (2009) *mAbs* 1:26-28). CH2 molecules can be made into binding proteins (e.g., binding to another molecule) by altering one or more of their loop regions through mutagenesis or CDR ("Complementarity Determining Region") grafting. CH2 molecules distribute in the body differently from antibodies due to their small size and retention of FcRn binding. To improve stability, CH2 molecules have been modified to include additional disulfide bonds, deletion of N-terminal amino acids, and/or deletion of C-terminal amino acids. Prior to the present disclosure, no attempt has been made to alter framework residues of an isolated CH2 domain to enhance stability, reduce immunogenicity, or reduce the likelihood of aggregation.

SUMMARY OF THE DISCLOSURE

One aspect of the disclosure is directed to isolated engineered CH2 domain molecules. The engineered CH2 domain molecules include four framework regions (FR1, FR2, FR3, and FR4) and three loop regions (L1, L2 and L3) located between FR1-FR2, FR2-FR3 and FR3-FR4, respectively, and include at least one amino acid substitution in at least one of the framework regions as compared to a template CH2 domain molecule.

In some embodiments, a template CH2 domain molecule comprises the amino acid sequence of SEQ ID NO: 1, which sequence differs from the wild type human CH2 domain of SEQ ID NO: 20 by lacking the six amino acids at the N-terminus. In some embodiments, a template CH2 domain molecule comprises the amino acid sequence of SEQ ID NO: 12 which has identical framework regions as SEQ ID NO: 1, but differs from SEQ ID NO: 1 in the loop regions.

Unless indicated otherwise, the amino acid numbering of a CH2 domain molecule is based on the template CH2 domain molecule of SEQ ID NO: 1.

In some embodiments, an engineered CH2 domain molecule includes 1-3 amino acid substitutions in the framework 1 region. In some embodiments, an engineered CH2 domain molecule includes an amino acid substitution of Val to Phe at position 27 (V27F) in the framework 1 region. In some embodiments, an engineered CH2 domain molecule includes an amino acid substitution of Leu to Met at position 15 (L15M) in the framework 1 region.

In some embodiments, an engineered CH2 domain molecule includes 1-3 amino acid substitutions in the framework 2 region. In some embodiments, an engineered CH2 domain molecule includes an amino acid substitution of Val to Ala at position 46 (V46A), or Asn to His at position 50 (N50H) in the framework 2 region.

In some embodiments, an engineered CH2 domain molecule includes 1-3 amino acid substitutions in the framework 3 region. In some embodiments, an engineered CH2 domain molecule includes an amino acid substitution of Lys to Thr at position 84 (K84T) in the framework 3 region. In some embodiments, an engineered CH2 domain molecule includes an amino acid substitution of Leu to Ser at position 73 (L73S) in the framework 3 region.

In some embodiments, an engineered CH2 domain molecule includes 1-3 amino acid substitutions in the framework 4 region. In some embodiments, an engineered CH2 domain molecule includes an amino acid substitution of Ala to Asp at position 103 (A103D) in the framework 4 region. In some embodiments, an engineered CH2 domain molecule includes an amino acid substitution of Glu to Gln at position 97 (E97Q) in the framework 4 region.

In some embodiments, an engineered CH2 domain molecule includes amino acid substitutions V27F, K84T and A103D; and in certain embodiments, the engineered CH2 domain molecule includes at least one additional amino acid substitution selected from the group consisting of Leu to Met at position 15 (L15M) in the framework 1 region, Val to Ala at position 46 (V46A) in the framework 2 region, Asn to His at position 50 (N50H) in the framework 2 region, Leu to Ser at position 73 (L73 S) in the framework 3 region, and Glu to Gln at position 97 (E97Q) in the framework 4 region.

In some embodiments, in an engineered CH2 domain molecule, the framework 1 region consists of an amino acid sequence of GPSVFLFPPKPKDT(L,M)MISRTPEVTCVFV (SEQ ID NO: 8), the framework 2 region consists of an amino acid sequence of KFNWYVDG(V,A)EVH(N,H)AKTKPR (SEQ ID NO: 9), the framework 3 region consists of an amino acid sequence of YRVVSVLTV(L,S)HQDWLNGKEYTCKV (SEQ ID NO: 10), and the framework 4 region consists of an amino acid sequence of (E,Q)KTISKDK ((SEQ ID NO: 11).

In some embodiments, in an engineered CH2 domain molecule, the loop 1, loop 2 and loop 3 are identical with the loop 1, loop 2 and loop 3 of the template CH2 domain molecule of SEQ ID NO: 1.

In some embodiments, in an engineered CH2 domain molecule, the loop 1, loop 2 and loop 3 are identical with the loop 1, loop 2 and loop 3 of the template CH2 domain molecule of SEQ ID NO: 12 (B11).

In some embodiments, an engineered CH2 domain molecule further includes at least one amino acid substitution, addition or deletion in one of loop 1, loop 2, or loop 3, as compared to a wild type CH2 domain or a template CH2 domain molecule, in addition to amino acid substitution(s) in one or more of the framework regions.

In some embodiments, an engineered CH2 domain molecule further includes at least one amino acid addition at the N-terminus, C-terminus or both termini, as compared to a wild type CH2 domain or a template CH2 domain molecule, in addition to amino acid substitution(s) in one or more of the framework regions.

In specific embodiments, an engineered CH2 domain molecule comprises an amino acid sequence selected from the group consisting of SEQ ID NOS: 3-7 and SEQ ID NOS: 22-26.

The engineered CH2 domain molecules disclosed herein exhibit enhanced stability and/or solubility as compared to a wild type CH2 domain molecule or a template CH2 domain molecule. In some embodiments, an engineered CH2 domain molecule has a melting temperature (Tm) higher than 62° C. In some embodiments, an engineered CH2 domain molecule exhibits improved solubility as compared to a wild type CH2 domain molecule or a template CH2 domain molecule. The engineered CH2 domain molecules disclosed herein also bind FcRn (e.g., human FcRn).

Another aspect of the disclosure is directed to a library of modified CH2 domain molecules, wherein for each modified CH2 domain molecule in the library, the framework 1 region consists of an amino acid sequence of GPSVFLFPPKPKDT(L,M)MISRTPEVTCVFV (SEQ ID NO: 8), the framework 2 region consists of an amino acid sequence of KFNWYVDG(V,A)EVH(N,H)AKTKPR (SEQ ID NO: 9), the framework 3 region consists of an amino acid sequence of YRVVSVLTV(L,S)HQDWLNGKEYTCKV (SEQ ID NO: 10), and the framework 4 region consists of an amino acid sequence of (E,Q)KTISKDK (SEQ ID NO: 11); wherein the modified CH2 domain molecules in the library differ from one another in the loop 1, loop 2, and/or loop 3 region, and differ from a wild type or a template CH2 domain molecule in the loop 1, loop 2, and/or loop 3 region by at least one amino acid substitution, deletion, or addition. In some embodiments, loop 3 of each CH2 domain molecule in the library comprises the amino acid sequence of SNKALPAPI (SEQ ID NO: 15). In some embodiments, the loop 1 region of each member in the library comprises an amino acid sequence selected from the group consisting of SEQ ID NO: 13, SEQ ID NO: 16 and SEQ ID NO: 18. In some embodiments, the loop 2 region of each member in the library comprises an amino acid sequence selected from the group consisting of SEQ ID NO: 14, SEQ ID NO: 17 and SEQ ID NO: 19.

Still another aspect of the disclosure is directed to a method of identifying a CH2 domain molecule that binds to a target antigen. The method includes the steps of contacting the library described herein with a target antigen and identifying a CH2 domain molecule from the library that binds to the target antigen.

BRIEF DESCRIPTION OF THE DRAWINGS

The patent or application file contains at least one drawing executed in color. Copies of this paper or patent application publication with color drawing(s) will be provided by the Office upon request and payment of the necessary fee.

FIG. 4 sets forth, from top to bottom, the amino acid sequences of a template CH2 domain molecule of SEQ ID NO: 1, a template CH2 domain molecule of SEQ ID NO: 2, abdurins ("ABD") 06-10 (SEQ ID NOS: 22-26, respectively), a template CH2 domain molecule designated as "B11" (SEQ ID NO: 12), and ABD 01-05 (SEQ ID NOS: 3-7, respectively). The FR1, FR2, FR3 and FR4 regions are indicated by underlines, and the framework region amino acid substitutions relative to the template molecule of SEQ ID NO: 1 are indicated in bold. The melting temperature (Tm), the Kd's for FcRn binding and soluble expression levels of the template (human) CH2 domain molecule of SEQ ID NO: 1, the template (Macaque) CH2 domain molecule of SEQ ID NO: 2, and B11 (SEQ ID NO: 12), and CH2 domain molecules ABD 01-05 are also summarized and shown at the bottom.

DETAILED DESCRIPTION

Figure 1:
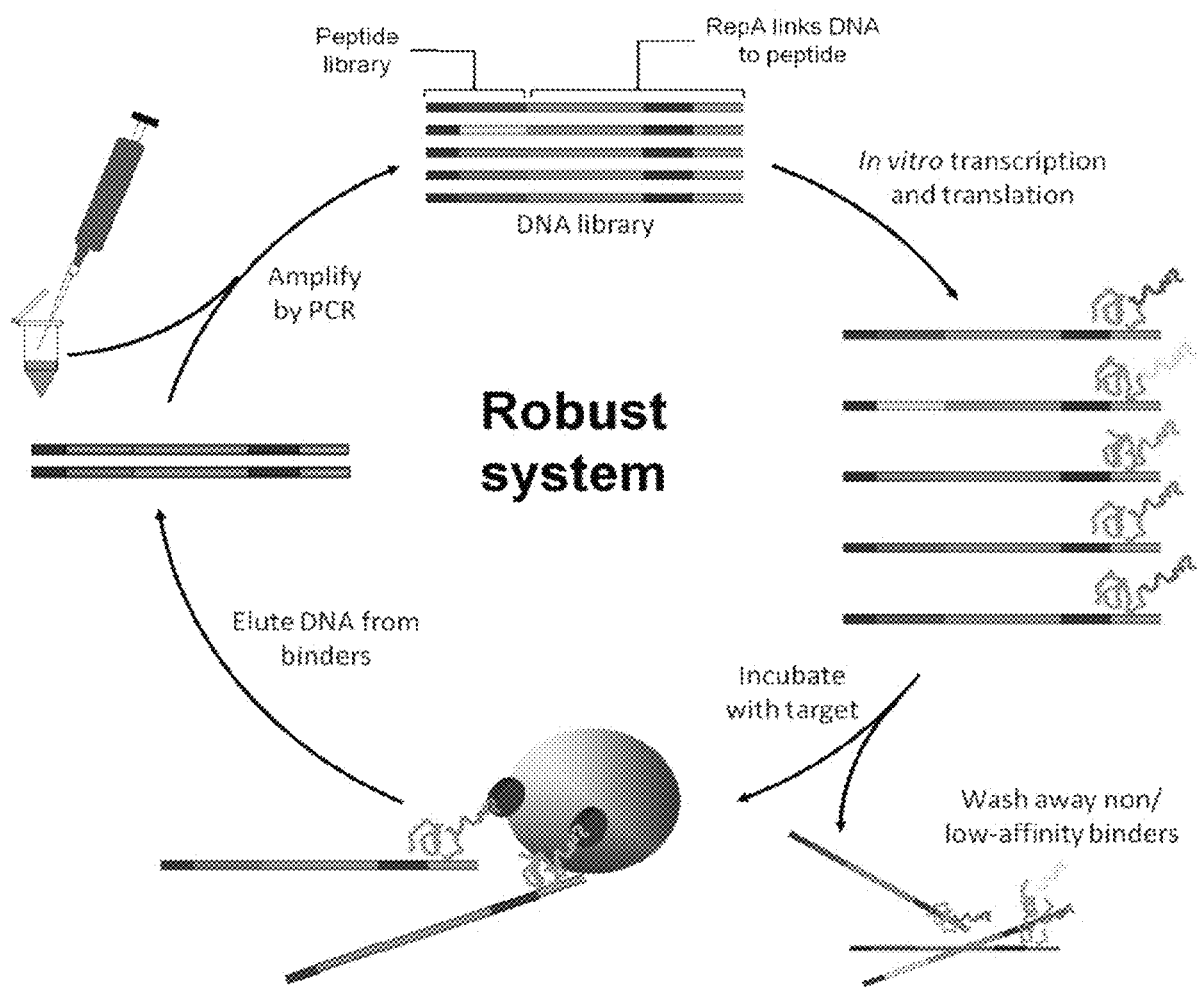
FIG. 1 illustrates the steps of the CIS DNA Display system used to screen for clones from seven constructed libraries.

This invention is predicated at least in part on the discovery that certain amino acid mutations within the framework regions of a CH2 domain molecule result in significantly improved stability of the molecule. Accordingly, CH2 domain molecules containing such stability conferring amino acids, as well as use of such molecules to generate CH2 libraries for screening for binders to specific targets, are provided in this disclosure.

CH2 Domain Molecules & Scaffolds

As used herein, the terms "CH2 scaffold", "CH2 domain", and "CH2 domain molecule" are used interchangeably and refer to a polypeptide that retains substantially the structural characteristic of a wild type CH2 domain and retains at least the FcRn binding characteristics of a wild type CH2 domain. A CH2 domain molecule includes, for example, both isolated CH2 domains of naturally occurring immunoglobulins ("wild type CH2 domain molecules"), template CH2 domain molecules, and engineered CH2 domain molecules containing amino acid modifications as compared to a wild type CH2 domain. Unless noted otherwise, the immunoglobulin can be IgG, IgA, IgD, IgE or IgM. Examples of wild type CH2 domains include the wild type human CH2 domain of SEQ ID NO: 20 and the wild type Macaque CH2 domain of SEQ ID NO: 21.

The term "a template CH2 domain molecule" refers to a CH2 domain molecule that serves as a starting molecule against which further amino acid modifications are made or compared. Examples of template CH2 domain molecules include (i) a CH2 domain molecule consisting of SEQ ID NO: 1, which differs from the wild type human CH2 domain of SEQ ID NO: 20 by lacking the six amino acids at the N-terminus; (ii) a CH2 domain molecule consisting of SEQ ID NO: 2, which differs from the wild type Macaque CH2 domain of SEQ ID NO: 22 by lacking the six amino acids at the N-terminus; and (iii) a CH2 domain molecule consisting of SEQ ID NO: 12, also referred to herein as "B11", which differs from SEQ ID NO: 1 only in the loop regions. Isolated CH2 domain molecules consisting of SEQ ID NO: 1, SEQ ID NO: 2, SEQ ID NO: 20 and SEQ ID NO: 22, respectively, do not bind to antigens other than those that the CH2 domain may normally bind in the context of an Ig molecule, e.g., FcRn, Fcγ and complement. B11, on the other hand, includes altered loops to enable EphA2 receptor binding and loses at least some other natural CH2 domain binding, such as that to Fcγ, except for FcRn binding.

By "retaining substantially the functional characteristic of a wild type CH2 domain" is meant that a CH2 domain molecule substantially retains at least the FcRn binding characteristics of a wild type CH2 domain.

A wild type CH2 domain is a polypeptide composed of a 3-stranded sheet containing strands C, F, and G, packed against a 4-stranded sheet containing strands A, B, D, and E. The β-strands, parallel to each other, are connected by loops of unstructured amino acid sequences. The CH2 domain 3-dimensional structure is stabilized by hydrogen bonding, by hydrophobic interactions, and by a disulfide bond.

A "loop region" of a CH2 domain refers to the portion of the protein located between regions of β-strands. For example, each CH2 comprises seven β-strands, A to G, oriented from the N- to C-terminus. A CH2 comprises six loop regions: Loop 1, Loop 2, Loop 3, Loop A-B, Loop C-D and Loop E-F. Loops A-B, C-D and E-F are located between β-strands A and B, C and D, and E and F, respectively. Loops 1, 2 and 3 are located between β-strands B and C, D and E, and F and G, respectively. These loops in a natural CH2 domain are often referred to as structural loops.

The term "framework region" as used herein refers to amino acid sequences outside of loops 1, 2 and 3; i.e., amino acid sequences interposed between loops 1-2 and between loops 2-3, as well as amino acid sequences N-terminal to loop 1 and C-terminal to loop 3. A CH2 domain contains four framework regions, referred herein as FR1, FR2, FR3 and FR4. The framework regions in a wild type CH2 domain serve to hold loops 1-3 in an appropriate orientation for their usual functions, and also form β-strand structures.

By "retaining substantially the structural characteristic of a wild type CH2 domain" is meant that a CH2 domain molecule substantially preserves the beta barrel configuration (i.e., the 3-stranded sheet containing strands C, F, and G, packed against the 4-stranded sheet containing strands A, B, D, and E) of a wild type CH2 domain (such as the wild type human CH2 domain as set forth in SEQ ID NO: 20, or the wild type Macaque CH2 domain as set forth in SEQ ID NO: 21). That is, the modifications in an engineered CH2 molecule relative to a wild type CH2 molecule preferably do not disrupt any or most of the hydrogen bonding, hydrophobic interactions, and the disulfide bond, which collectively hold the beta barrel configuration in the wild type CH2 molecule. Amino acid residues involved in maintaining the beta barrel structure are known in the art, including the residues that form hydrogen bonding, hydrophobic interactions, and the disulfide bond, typically residues in the framework regions of CH2 molecules.

In specific embodiments, the residues critical to maintaining the beta barrel structure in a natural occurring CH2 domain are maintained and not modified. Modifications at or near the terminal regions of a native CH2 may be more tolerable (i.e., less likely to disrupt the structure or conformation of a native CH2) as compared to modifications to other regions. For example, CH2 molecules that differ from a wild type CH2 domain by lacking the six amino acids at the N-terminus of the wild type CH2 domain (e.g., SEQ ID NO: 1 or SEQ ID NO: 2) are expected to maintain the beta barrel structure in the natural occurring CH2 domain. In some embodiments, with the exception of the deletion of the six amino acids at the N-terminus of a wild type CH2 domain, the framework residues are substantially not modified; for example, the lengths of framework regions are not modified and not more than 15%, or 10% or 5% of the framework residues are substituted in an engineered CH2 scaffold, as compared to a wild type CH2 domain or a template CH2 domain that only differs from a wild type CH2 domain by lacking the six amino acids at the N-terminus. Where modifications are made to framework residues, the modifications substantially do not affect the structural or functional characteristics of the engineered CH2 scaffold; e.g., the engineered CH2 scaffold assumes substantially the same three-dimensional conformation. In various embodiments, the CH2 scaffolds disclosed herein contain alterations in one or more, e.g., 1-5 (i.e., 1, 2, 3, 4 or 5), or 1-3 (i.e., 1, 2 or 3), framework amino acids to confer improved stability of the resulting CH2 scaffold, without involving the formation of additional disulfide bonds.

For the template CH2 domain molecule of SEQ ID NO: 1, framework region 1 is composed of amino acids G1-V28 (i.e., 28 amino acids), loop 1 is composed of D29-V37 (i.e., 9 amino acids), framework region 2 is composed of K38-R56 (i.e., 19 amino acids), loop 2 is composed of E57-T63 (i.e., 7 amino acids), framework region 3 is composed Y64-V87 (24 amino acids), loop 3 is composed of S88-I96 (i.e., 9 amino acids), and framework region 4 is composed of E97-K104 (8 amino acids). In all cases the junction between a framework region and a loop can be shifted by 1-2 amino acids from what is identified above.

In some embodiments, an engineered CH2 scaffold may comprise substantially the same loop regions as a wild type CH2 domain (e.g., SEQ ID NOS: 20 and 21), a template CH2 domain (SEQ ID NO: 1, SEQ ID NO: 2, or SEQ ID NO: 12), or loop regions having lengths that closely match the lengths of the loop regions as a wild type or template CH2 domain (e.g., loops 1-3 having 9, 7 and 9 amino acids, respectively, or plus or minus one or two amino acids. In some embodiments, an engineered CH2 scaffold can include one or more mutations in a loop region as compared to a wild type or template CH2 domain. Such loop mutations can include one or more amino acid deletions, additions or substitutions. In some embodiments, an engineered CH2 scaffold may have one or more loop regions replaced in full or in part with a CDR or a functional fragment of a CDR, or with a donor loop from a donor molecule.

Wild type CH2 domain molecules are small in size, usually less than 15 kD. Engineered CH2 domain molecules can vary in size and may have a molecular weight up to 22 kDa. In some embodiments, engineered CH2 domain molecules substantially retain the same loop regions of a wild type CH2 domain or a template CH2 domain molecule. In other embodiments wherein one or more loop regions of a wild type CH2 domain or a template CH2 domain molecule have been modified or replaced by one or more heterologous sequences (such as a CDR or a donor loop), the engineered CH2 scaffold may differ in size from the wild type CH2 domain or the template molecule, depending on the length of the modified loops. In some embodiments, an engineered CH2 domain molecule has a molecular weight not more than 22, 21, 20, 19, 18, 17, 16, or 15 kD.

The CH2 scaffolds disclosed herein may be glycosylated or unglycosylated. For example, a CH2 scaffold can be expressed in an appropriate yeast, insect, plant or mammalian cell to allow glycosylation of the molecule at one or more natural or engineered glycosylation sites in the protein. A method of homogenously or nearly homogenously glycosylating recombinant proteins has been developed in genetically-engineered yeast (Jacobs et al., Nature Protocols 1(4):58-70, 2009). The glycans added to the protein may be the same as occur naturally or may be forms not usually found on human glycoproteins. Non-limiting examples include Man5, GnMan5, GalGnMan5 GnMan3, GalGnMan3, Gn2Man3, Gal2Gn2Man3. In vitro reactions may be used to add additional components (such as sialic acid) to the glycans added in the recombinant production of the glycoprotein. Addition of different glycans may provide for improvements in half-life, stability, and other pharmaceutical properties.

Engineered CH2 Domain Molecules or Scaffolds
Modifications Defined

As used herein, the term "modified" or "modification" refer to changes made to a starting CH2 domain molecule (e.g., a wild type or template CH2 domain molecule), and can include one or more amino acid deletions, additions or substitutions, covalent bonding with another component, post-translational modification (e.g., acetylation, glycosylation, the like, or a combination thereof), the like, or a combination thereof. Modifications to CH2 scaffolds can be made through random mutagenesis, mutagenesis based on rational design, as well as through selection of mutant CH2 scaffolds, e.g., from mutant CH2 libraries.

Conservative Substitutions

Conservative amino acid substitutions include the substitution of a non-polar (hydrophobic) residue such as I, V, L or M for another; the substitution of one polar (hydrophilic) residue for another polar residue, such as R for K, Q for N, G for S, or vice versa; and the substitution of a basic residue such as K, R or H for another, or the substitution of one acidic residue such as D or E for another. Conservative amino acid substitutions generally do not substantially affect or decrease an activity or antigenicity of a polypeptide. For example, a polypeptide can include at most about 1, at most about 2, or at most about 5 conservative substitutions and specifically bind an antibody that binds the original polypeptide. Conservative substitutions generally maintain (a) the structure of the polypeptide backbone in the area of the substitution, for example, as a sheet or helical conformation, (b) the charge or hydrophobicity of the molecule at the target site, and/or (c) the bulk of the side chain. Specific examples of conservative substitutions include: Ala-Ser; Arg-Lys; Asn-Gln; Asp-Glu; Gln-Asn; Glu-Asp; Ile-Leu or Val; Leu-Ile or Val; Lys-Arg; Met-Leu or Ile; Phe-Met, Leu, or Tyr; Ser-Thr; Thr-Ser; Trp-Tyr; Tyr-Trp or Phe; and Val-Ile or Leu.

In contrast, examples of non-conservative substitutions include the substitution of a non-polar (hydrophobic) residue such as I, V, L, A, M for a polar (hydrophilic) residue such as C, Q, D, K and/or vice versa. The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histadine, is substituted for (or by) an electronegative residue, for example, glutamate or aspartate; or (d) a residue having a bulky side chain, for example, phenylalanine, is substituted for (or by) one not having a side chain, for example, glycine.

Modifications to Framework Regions

In some embodiments, the engineered CH2 molecules include modifications to the framework regions of a wild type or template CH2 domain molecule, particularly modifications that result in enhanced stability and/or solubility of the engineered CH2 molecules. In some embodiments, the modification includes at least one amino acid substitution in at least one of the framework regions.

In some embodiments, the modification to the engineered CH2 domain molecule include substitutions of 1-3 amino acids in the framework 1 region. In some embodiments, the modification includes an amino acid substitution of Val to Phe at position 27 (V27F) in the framework 1 region relative to the framework 1 region in a template CH2 domain molecule such as SEQ ID NO: 1, with the amino acid numbering based on the wild type human CH2 molecule of SEQ ID NO: 1. In some embodiments, the modification includes an amino acid substitution of Leu to Met at position 15 (L15M) in the framework 1 region relative to the framework 1 region in a template CH2 domain molecule such as SEQ ID NO: 1. In some embodiments, the modification includes an amino acid substitution of Val to Lys at position 28 (V28K) relative to the framework 1 region in a template CH2 domain molecule such as SEQ ID NO: 1. In particular embodiments, an engineered CH2 molecule includes a framework 1 region having the amino acid sequence of GPSVFLFPPKPKDT(L or M)MISRTPEVTCVFV (SEQ ID NO: 8).

In some embodiments, the modification includes 1-3 amino acid substitutions in the framework 2 region. In specific embodiments, the modification includes an amino acid substitution of Val to Ala at position 46 (V46A), relative to the framework 2 region in a template CH2 domain molecule such as SEQ ID NO: 1. In specific embodiments, the modification includes an amino acid substitution of Asn to His at position 50 (N50H), relative to the framework 2 region in a template CH2 domain molecule such as SEQ ID NO: 1. In particular embodiments, an engineered CH2 molecule includes a framework 2 region having the amino acid sequence of KFNWYVDG(V or A)EVH(N or H)AKTKPR (SEQ ID NO: 9).

In some embodiments, the modification includes 1-3 amino acid substitutions in the framework 3 region. In specific embodiments, the modification includes an amino acid substitution of Lys to Thr at position 84 (K84T) in the framework 3 region, relative to the framework 3 region in a template CH2 domain molecule such as SEQ ID NO: 1. In some embodiments, the modification includes an amino acid substitution of Leu to Ser or Lys at position 73 (L73S or L73K), relative to the framework 3 region in a template CH2 domain molecule such as SEQ ID NO: 1. In particular embodiments, an engineered CH2 molecule includes a framework 3 region having the amino acid sequence of YRVVSVLTV(L or S)HQDWLNGKEYTCKV (SEQ ID NO: 10).

In some embodiments, the modification includes 1-3 amino acid substitutions in the framework 4 region. In specific embodiments, the modification includes an amino acid substitution of Ala to Asp at position 103 (A103D) in the framework 4 region, relative to the framework 4 region in a template CH2 domain molecule such as SEQ ID NO: 1. In some embodiments, the modification includes an amino acid substitution of Glu to Gln at position 97 (E97Q), relative to the framework 4 region in a template CH2 domain molecule such as SEQ ID NO: 1. In particular embodiments, an engineered CH2 molecule includes a framework 4 region having the amino acid sequence of (E or Q)KTISKDK (SEQ ID NO: 11).

In specific embodiments, the modification includes amino acid substitutions V27F, K84T and A103D, relative to a template CH2 molecule such as SEQ ID NO: 1. In particular embodiments, the modification includes one or more additional amino acid substitutions relative to a template CH2 molecule such as SEQ ID NO: 1, selected from the group consisting of Leu to Met at position 15 (L15M) in the framework 1 region, Val to Ala at position 46 (V46A) in the framework 2 region, Asn to His at position 50 (N50H) in the framework 2 region, Leu to Ser at position 73 (L73 S) in the framework 3 region, and Glu to Gln at position 97 (E97Q) in the framework 4 region.

In certain embodiments, an engineered CH2 domain molecule includes a framework 1 region consisting of an amino acid sequence of GPSVFLFPPKPKDT(L,M)MISRTPE-VTCVFV (SEQ ID NO: 8), a framework 2 region consisting of an amino acid sequence of KFNWYVDG(V,A)EVH(N,H)AKTKPR (SEQ ID NO: 9), a framework 3 region consisting of an amino acid sequence of YRVVSVLTV(L,S)HQDWLNGKEYTCKV (SEQ ID NO: 10), and the framework 4 region consisting of an amino acid sequence of (E,Q)KTISKDK (SEQ ID NO: 11).

Modifications to Loop Regions

In some embodiments, in an engineered CH2 domain molecule, the loop 1, loop 2 and loop 3 are identical with the loop 1, loop 2 and loop 3 of the wild type human or Macaque CH2 domain molecules (SEQ ID NOS: 20-21), the template CH2 domain molecule of SEQ ID NO: 1 or SEQ ID NO: 12.

In some embodiments, in addition to modifications to the framework regions for improved stability and/or solubility, an engineered CH2 scaffold may include a modification(s) to one or more loop regions relative to a wild type CH2 scaffold or a template CH2 domain molecule.

In some embodiments, one or more of L1, L2, and/or L3 loops of a native CH2 scaffold, a template CH2 domain molecule, or an engineered CH2 scaffold having stability enhancing modifications within one or more of the framework regions, can include one or more amino acid additions, deletions or substitutions. Desirable mutations in one or more loop regions of a CH2 scaffold can be made through direct mutagenesis, or obtained by constructing libraries having random mutations at some or all positions of one or more loop regions of the CH2 scaffold, and subsequently screening the libraries for scaffolds that meet certain selection criteria (e.g., stability, solubility, FcRn binding, and target binding, and the like).

In some embodiments, one or more of L1, L2, and/or L3 loops of a native or template CH2 scaffold have been replaced with donor loops, as described in WO 2013/119903 (Bramhill et al., Research Corporation Technologies, Inc.). Loops from a database of domains (the "donor loops") may be transferred to a starting acceptor CH2 scaffold, e.g., a wild type CH2 scaffold or an engineered CH2 scaffold having stability enhancing modifications within one or more of the framework regions. The donor loops may be chosen based on, for example, that the chosen donor molecule may have structural resemblance to a CH2 scaffold and also have three structural loops with one or more of the structural loops having a length that is similar (but not necessarily identical) to that of a loop in the acceptor CH2 scaffold. Without wishing to limit the present invention to any theory or mechanism, a careful rational transfer of such compatible structural loops from a selected donor may ensure preservation of the stereochemistry and surface topology of the antigen binding region of the donor molecule. Also, preservation of interactions among the loops and between the loops and the proximal β strands may lead to molecules that have desirable biophysical and biochemical properties (e.g., stability, solubility). Compatible loops may help to maintain affinity with the target. Variations in loop lengths may provide recognition with different types of antigens.

In some embodiments, donor molecules are chosen based on having two of three loops having lengths that closely match the corresponding two loops in an acceptor CH2 scaffold. The term "closely match" is meant to include an exact match, plus or minus one amino acid, plus or minus two amino acids, plus or minus three amino acids, plus or minus four amino acids, plus or minus five amino acids. For example, if the L2 loop of a CH2 scaffold is to be replaced, a donor molecule may be selected because its L1 loop and L3 loop closely match the length of the L1 loop and L3 loop, respectively, of the CH2 scaffold, and after the donor molecule is chosen the L2 loop of that chosen donor molecule is used to replace the L2 loop of the CH2 scaffold. In some embodiments, if a CH2 scaffold's L1 loop is to be replaced, a donor molecule may be selected because its L2 loop and L3 loop closely match (e.g., an exact match, plus or minus one amino acid, plus or minus two amino acids, plus or minus three amino acids, plus or minus four amino acids, plus or minus five amino acids, plus or minus more than five amino acids, etc.) the length of the L2 loop and L3 loop, respectively, of the CH2 scaffold, and after the donor molecule is chosen the L1 loop of that chosen donor molecule is used to replace the L1 loop of the CH2 scaffold. In some embodiments, if the L3 loop of a CH2 scaffold is to be replaced, a donor molecule may be selected because its L1 loop and L2 loop closely match (e.g., an exact match, plus or minus one amino acid, plus or minus two amino acids, plus or minus three amino acids, plus or minus four amino acids, plus or minus five amino acids, plus or minus more than five amino acids, etc.) the length of the L1 loop and L2 loop, respectively, of the CH2 scaffold, and after the donor molecule is chosen the L3 loop of that chosen donor molecule is used to replace the L3 loop of the CH2 scaffold.

In some embodiments, a donor molecule may be chosen based on the length of one of its three loops that closes matches a corresponding loop in an acceptor CH2 scaffold. For example, a donor molecule can be chosen based on having a L1 loop that has a length closely matching the L1 loop of a CH2 scaffold, where the L2 and L3 loops from the donor molecule replace the L2 and L3 loops of the acceptor CH2 scaffold.

In some embodiments, a donor molecule may be chosen based on the lengths of all three of its loops that closes match the corresponding three loops in an acceptor CH2 scaffold.

Selection of donor molecules (and donor loops) in this manner (e.g., "matching" lengths of one or two or all three of the loops) may help the resulting engineered CH2 scaffold retain substantially the structural features of the starting CH2 scaffold (e.g., a wild type CH2 scaffold or other engineered CH2 scaffold). Maintaining structural resemblance to the starting CH2 scaffold may allow for general retention (or even improvement) of certain properties of the molecule, for example stability (see below).

In some embodiments, the donor loop that actually replaces the loop of a CH2 scaffold may or may not necessarily have a length that is identical or similar to that of the loop it replaces. As an example, if the L2 loop of a CH2 scaffold is replaced with a donor L2 loop from a donor molecule, the donor L2 loop may have a longer length than the L2 loop of the CH2 scaffold (and the additional length may be that the donor L2 loop naturally has more amino acids than the L2 loop of the CH2 scaffold or amino acids are added to the donor L2 loop, for example).

In some embodiments, the donor loop that actually replaces the loop of a CH2 scaffold has a length that is identical or similar to, or closely matches, that of the loop it replaces.

The donor molecule choice is generally due to the 3D architecture of the 0 sheets sandwich present in the domains of the donor molecule, which are generally similar to the 3D fold of a CH2 scaffold. A beta strand leads up to the L2 loop in the V domains of antibodies. The corresponding portion in a CH2 domain does not have the geometry and stereochemistry typical of a beta strand, but is closer to a random coil. Despite this difference, the overall dispositions of the three loops, namely L1, L2 and L3, are preserved in the donor database molecules and the CH2 domains. The donor molecules may be obtained from a database of crystal structures or molecules, for example a database of crystal structures of Ig-like molecules, or a database of crystal structures of V-like domains of immunogbulins and related molecules. However, the donor molecules are not limited to V-like domains of immunoglobulins and related molecules. Any other peptide, not necessarily one of a V-like domain, may be contemplated for transfer onto a CH2 scaffold.

The V-domain generally corresponds to the crystal structure of the V-J region or V-D-J region of the immunoglobulin or T cell receptor chain. This single V-domain is designated as: VH (V-domain of an Ig-Heavy chain), VL (V-domain of an Ig-Light chain), V-kappa (V-domain of an Ig-Light-Kappa chain), V-lambda (V-domain of an Ig-Light-Lambda chain), V-alpha (V-domain of a TcR-Alpha chain), V-beta (V-domain of a TcR-Beta chain), V-gamma (V-domain of a TcR-Gamma chain), and V-delta (V-domain of a TcR-Delta chain). A V-like domain may correspond to a domain of similar 3D structure (beta-sandwich framework with CDR-like loops) as the V-domain for proteins other than immunoglobulin or T cell receptor chain.

Other Modifications

An engineered CH2 scaffold may comprise an amino acid addition of 1-5 amino acids, for example at its N-terminus, at its C-terminus, or at both termini.

Properties of Modified CH2 Domains

Stability, Solubility, Serum Half-Life

Stability is an important property of a protein, and it can determine the ability of the protein to withstand storage or transport conditions as well as affect the protein's half-life after administration (e.g., in serum).

In some embodiments, the engineered CH2 domain molecules disclosed herein have enhanced stability as a result of modifications made within one or more of the framework regions as disclosed above. Enhanced stability is reflected by a higher melting temperature, increased resistance to urea-induced unfolding, and/or increased solubility, relative to a CH2 molecule without the modification (e.g., a wild type CH2 domain or a template CH2 domain molecule).

In some embodiments, a CH2 domain molecule has a Tm higher than 61° C., 62° C., 63° C., 64° C., 65° C., 66° C., 67° C., 68° C., 69° C., 70° C., 71° C., 72° C., 73° C., 74° C., 75° C. or even 76° C.

In some embodiments, an engineered CH2 domain molecule has a soluble expression level from an *E. coli* expression system of at least 700, 800, 900, 1000, 1100, 1200, 1300, 1400, 1500, 1600, 1700, 1800, 1900, 2000 μg/mL or greater. In some embodiments, a CH2 domain molecule has a soluble expression level that is approximately the same as (i.e., within 5%, 10%, 15% or 20% deviation), or better (e.g., by 10%, 20%, 30%, 40%, 50%, 60%, 70%, 80%, 90%, 100% or greater) than a wild type CH2 domain or a template CH2 domain molecule expressed from the same expression system, such as an *E. coli* expression system, a phage system, a yeast system, an insect system, or a mammalian system.

An engineered CH2 domain molecule disclosed herein may have the same or enhanced serum (or blood) half-life as compared to a native CH2 domain or a template CH2 domain molecule. Serum half-life of an immunoglobulin is mediated in part by the binding of the $F_c$ region to the neonatal receptor FcRn. The alpha domain is the portion of FcRn that interacts with the CH2 domain (and possibly CH3 domain) of IgG, and possibly with IgA, and IgD or with the CH3 domain (and possibly CH4 domain) of IgM and IgE. Several studies support a correlation between the affinity for FcRn binding at pH 6.0 and the serum half-life of an immunoglobulin. The FcRn binding sites may be natural FcRn binding sites, and/or modified FcRn binding sites.

In some embodiments, a CH2 scaffold is adapted to bind to albumin or another serum protein, e.g., by including an albumin binding site. In some embodiments, a CH2 scaffold, comprises a pendant peptide that can bind albumin. In some embodiments, an albumin-binding CH2 scaffold further comprises one or more PEGs (polyethylene glycols) (e.g., dPEGs, i.e., discrete PEGs that are shorter and have relatively low molecular weight) for increase of half life.

In some embodiments, a CH2 domain molecule disclosed herein is bound to a stability scaffold that confers increased stability (e.g., serum half-life), for example a molecule that binds a serum component (such as albumin), a dextran or a polyethylene glycol (PEG), which is expected to inhibit clearance and increase circulating half-life.

In some embodiments, an engineered CH2 domain molecule is contained in a pharmaceutical composition for providing increased stability. Pharmaceutical compositions for antibodies and peptides are well known to one of ordinary skill in the art. For example, U.S. Pat. No. 7,648, 702 features an aqueous pharmaceutical composition suitable for long-term storage of polypeptides containing an Fc domain of an immunoglobulin.

Effector Molecule Binding

In some embodiments, an engineered CH2 domain molecule substantially retains the FcRn binding characteristics of a wild type CH2 domain molecule, e.g., by having binding affinity at pH 6.0 (reflected by the equilibrium dissociation constant Kd) that is within a 10%, 20%, 30%, 40%, or 50% deviation from the binding affinity of a wild type CH2 domain molecule.

Conjugates

In some embodiments, the modified CH2 domains described herein may be joined to a second molecule to form an immunoconjugate, wherein the second molecule is, for example, a detectable moiety, a toxin, an epitope binding protein, or a small molecule chemical compound.

Examples of toxins include, but are not limited to, abrin, ricin, *Pseudomonas* exotoxin (PE, such as PE35, PE37, PE38, and PE40), diphtheria toxin (DT), botulinum toxin, small molecule toxins, saporin, restrictocin, sarcin or gelonin, or modified toxins thereof. Other cytotoxic agents that may be attached to a CH2 scaffold include auristatins, maytansinoids, doxorubicin, and cytolytic peptides.

CH2 domain molecules can be linked to any of these agents through a linker. Examples of linkers include peptides, non-peptide moieties (e.g., a sugar moiety, cleavable and non-cleavable chemical linkers), and polyethylene glycols (PEGs), e.g., discrete PEGs (dPEGs).

Pharmaceutical Compositions

A CH2 domain molecule can be provided along with a pharmaceutically acceptable carrier in a pharmaceutical composition. Pharmaceutical compositions may comprise buffers (e.g., sodium phosphate, histidine, potassium phosphate, sodium citrate, potassium citrate, maleic acid, ammonium acetate, tris-(hydroxymethyl)-aminomethane (tris), acetate, diethanolamine, etc.), amino acids (e.g., arginine, cysteine, histidine, glycine, serine, lysine, alanine, glutamic acid, proline), sodium chloride, potassium chloride, sodium citrate, sucrose, glucose, mannitol, lactose, glycerol, xylitol, sorbitol, maltose, inositol, trehalose, bovine serum albumin (BSA), albumin (e.g., human serum albumin, recombinant albumin), dextran, PVA, hydroxypropyl methylcellulose (HPMC), polyethyleneimine, gelatin, polyvinylpyrrolidone (PVP), hydroxyethylcellulose (HEC), polyethylene glycol (PEG), ethylene glycol, dimethylsulfoxide (DMSO), dimethylformamide (DMF), hydrochloride, sacrosine, gamma-aminobutyric acid, Tween-20, Tween-80, sodium dodecyl sulfate (SDS), polysorbate, polyoxyethylene copolymer, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate, 2-O-beta-mannoglycerate, the like, or a combination thereof. The present invention is in no way limited to the pharmaceutical composition components disclosed herein, for example pharmaceutical compositions may comprise propellants (e.g., hydrofluoroalkane (HFA)) for aerosol delivery. U.S. Pat. No. 5,192,743 describes a formulation that when reconstituted forms a gel which can improve stability of a protein of interest (e.g., for storage).

Library Construction and Screening

In some embodiments, engineered CH2 scaffolds containing stability-enhancing modifications in one or more CH2 framework regions along with the loop regions of a wild type or template CH2 domain molecule (e.g., SEQ ID NOS: 1, 2, or 12) are used in construction of loop libraries, e.g., L1, L2, L3, L1 plus L2, L1 plus L3, L2 plus L3, or L1 plus L2 plus L3 mutant libraries.

The present description is further illustrated by the following example, which should not be construed as limiting in any way. The contents of all cited references (including literature references, issued patents, and published patent applications as cited throughout this application) are hereby expressly incorporated by reference.

Example—1

B11 is a CH2 domain molecule (SEQ ID NO: 12) that binds to the EphA2 receptor protein and is described in WO 2016/065258 A1. The following mutant libraries were constructed using B11.

Library 1 was generated by mutating residues on the exposed area typically hidden as a result of glycosylation and replacing with more charged residues.

Library 2 was generated by mutating non-critical residues in the hydrophobic core.

Library 3 was generated by mutating polar surface residues to improve the electrostatic ionic network on the surface (to reduce potential aggregation).

Library 4 was generated by mutating only those residues that appear in the wild type macaque CH2 domain which were different from the human CH2 domain.

Library 5 was generated by subjecting the framework regions to random mutagenesis.

Library 6 was generated by codon optimizing the initial 20 amino acids residues in order to improve expression.

Library 7 was generated by including scaffold mutations previously reported in the literature to improve stability and protease resistance of a CH2 domain embedded in an immunoglobulin molecule.

Figure 2:
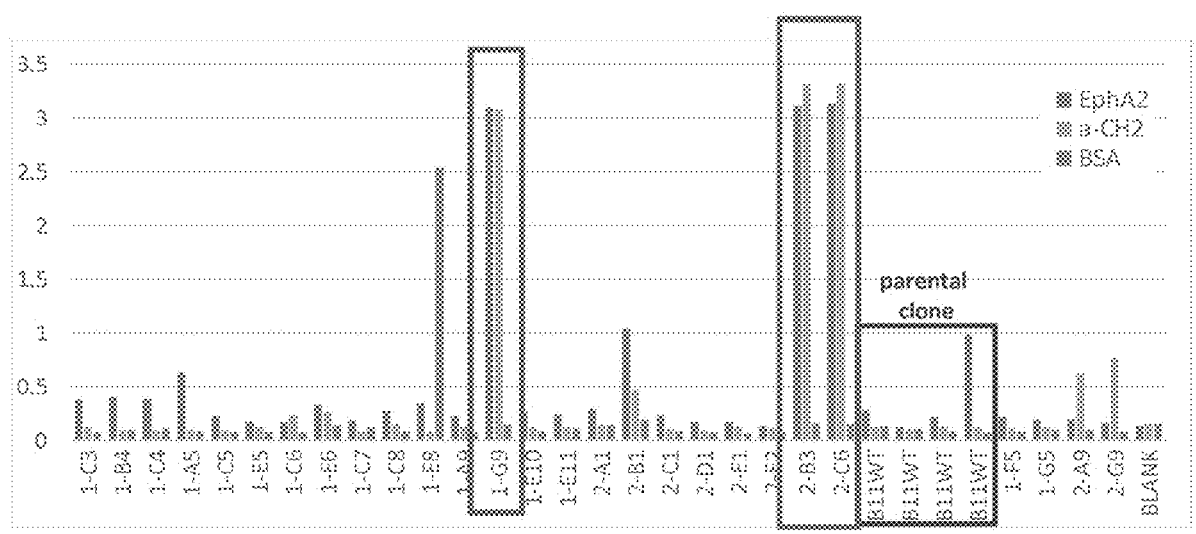
FIG. 2 are data for high temperature screens. The values on the y axis represent the amounts of DNA captured in nanograms. For each clone, binding to EphA2 receptor, binding by an antibody specific for a correctly folded CH2 domain ("a-CH2"), and to BSA were assessed and represented by bars from left to right. Clones identified within the left two boxes were clones encoding CH2 domain molecules with improved stability in the assays at high temperature as compared to the parental molecule (B11).

These libraries were all constructed and formatted into CIS DNA Display. CIS DNA Display is a molecular evolution tool, which is described in the literature (e.g., Odegrip et al., PNAS 101(9): 2806-2810 (2004); U.S. Pat. Nos. 7,842,476, 8,557,744 and 8,679,781) and also illustrated in FIG. 1. If all the libraries are pooled and used at the same time, the system can allow recombination events between libraries to create hybrids and unexpected pairings of mutations not otherwise anticipated. Because B11 originally bound to EphA2 receptor, the libraries were screened for proteins linked to cognate DNA that bound to EphA2 receptor after 3 hours of incubation at 45° C. In parallel, the same libraries were screened under the denaturing conditions of a high concentration (4M) urea. It was hypothesized that because proteins began to denature or unfold as temperature increased, proteins that still bound to EphA2 receptor at a high temperature (such as 45° C.) or with a high concentration of urea (e.g., 4M) would be very stable molecules at body temperature, 37° C. Binders that were isolated after binding at 45° C. or with 4M urea were sequenced to determine what mutations may have allowed this improved stability. FIG. 2 depicts an example of the data for these high temperature screens. Clones in the boxes labeled as 1-G9, 2-B3, and 2C6 were desired clones with improved stability. The y-axis represents the amount of DNA bound (in nanograms).

Once all the positive clones were sequenced, several dominating mutations were discovered in the majority of the clones. Single mutation clones were identified as well. The main families were:

1. Clones having four mutations: D44N/V46A/L73S/K84T

2. Clones having five mutations: L15M/V46A/N50H/L73S/A103T
3. Clones having a single mutation: V27F
4. Clones having V4I/V28L/A103P
5. Clones having one of the above sets of mutations, or some of the mutations in one of the above sets of mutations, or a combination thereof, sometimes with 1-2 additional mutations.

Additional clones were generated by mixing and matching among the identified mutations based on an understanding of the CH2 scaffold and to avoid generating any T cell epitopes. Clones were also generated by substituting certain identified substitution mutations with similar substituting amino acids.

Figure 3:
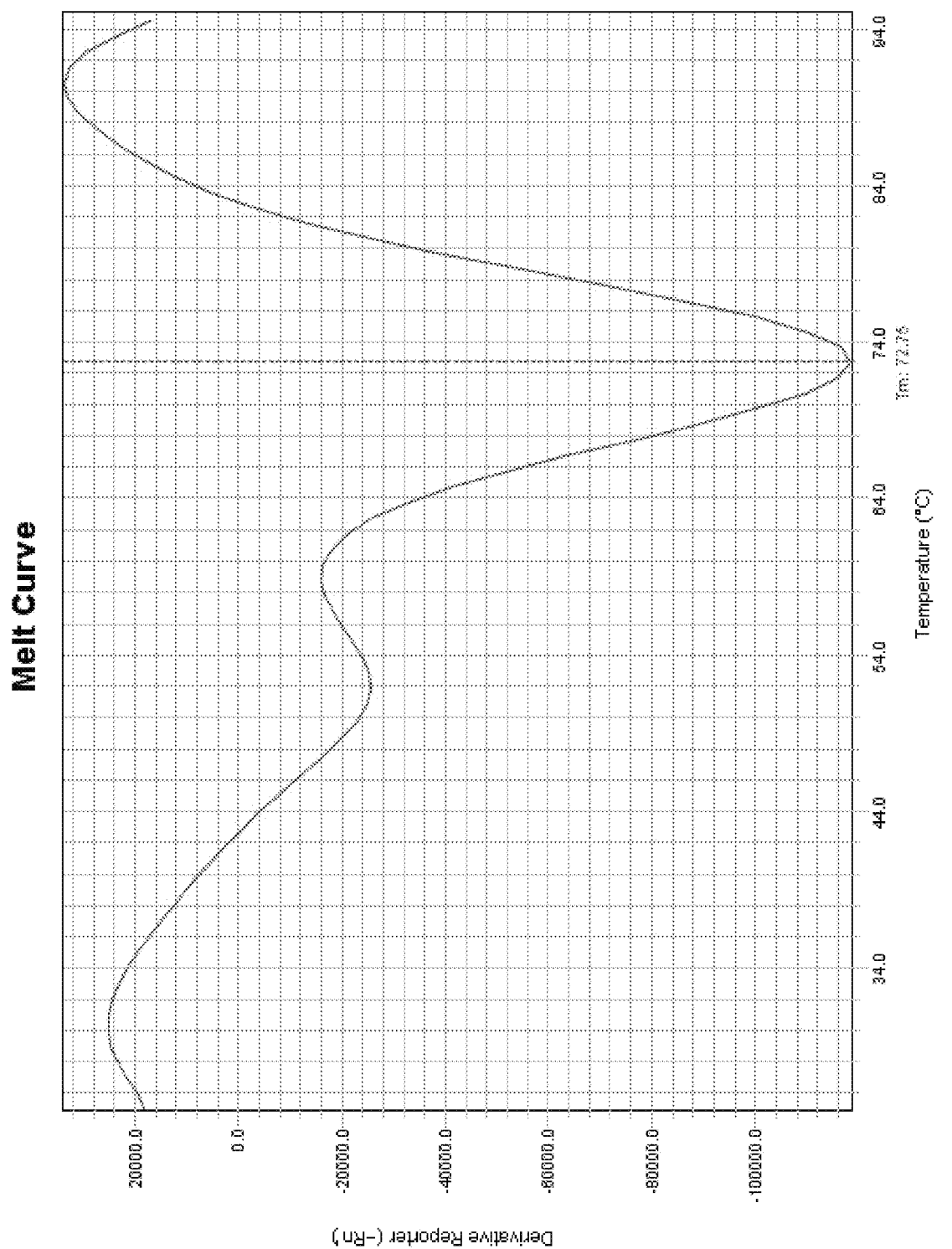
FIG. 3 illustrates Tm measurement for clone 9S41 (aka ABD01 in FIG. 4, V27F/K84T/A103D), showing a Tm of 72.75° C.

Approximately 100 different clones were expressed in *E. coli* and the expressed proteins were evaluated for expression levels, binding to EphA2 receptor and to FcRn, and melting temperature (Tm). Possible generation of a T cell epitope was also assessed. Test libraries were also made to test changes in the context of loop mutations to determine whether a clone encodes a scaffold that would tolerate changes in the loops. FcRn binding was measured using a Biacore assay on human recombinant FcRn protein. Tm was measured using both Differential Scanning Calorimetry and Circular Dichroism (also used for the assays in 4M urea). FIG. 3 shows measurement of Tm for clone 9S41 (V28F/K85T/A104D), showing Tm as 72.75° C. Protein expression was measured directly by measuring the amount of purified protein obtained from small scale fermentation in shake flasks and the results were summarized as µg/ml.

The 5 best scaffolds were selected which had a high melting temp (>70° C.) as compared to the melting temperature of B11 (56° C.), high expression in *E. coli* which suggests good solubility, folding and expression; were stable in 4M urea, stable in serum, and would tolerate changes in the loops (as summarized in FIG. 4). These molecules were designated as ABD01 to ABD05 (ABD for "abdurin"), and their sequences are set forth in SEQ ID NOS: 3-7 (see FIG. 4). The mutations in each of the 5 scaffolds were cloned into the shortened wild type human CH2 scaffold (SEQ ID NO: 1), and the resulting CH2 domain molecules were designated as (SEQ ID NOS: 22-26) (also shown in FIG. 4).

The methods used in the experiments described above are as follows.

Method and Procedure for Producing Abdurins in *E. coli*:
  Transform HB2151 or BL21, or other electrocompetent cells with expression plasmid.
  Grow pre-inoculum overnight at 37° C. in 2×Ty/Amp+2% Glucose.
  Dilute pre-inoculum 1:100 in the 1 L2×Ty/Amp.
  Induce with 1 mM IPTG at OD 0.8 and grow cells overnight at 30° C.
  Collect cells and suspend the pellet in 50 ml Periplasm Lysis buffer (25 mM Tris pH 8.0, 500 mM NaCl, 2 mM MgCl2, Complete EDTA-free Protease Inhibitor Cocktail). Add 0.1% Lysozyme or 0.5 mU/ml Polymyxin B (stock solution 0.5 U/ml).
  Incubate 30 min at room temperature under rotation.
  Centrifuge 16000 rpm 30 min 4° C.
  Transfer supernatant on 2.5 ml NiNTA resin pre-incubated in Periplasm Lysis buffer without Protease Inhibitor.
  Incubate 1 hr at 4° C. under rotation.
  Collect the resin by centrifugation at 4200 rpm, 4° C., 2 min.
  3× wash with 20 CV (50 ml) of 30 mM imidazole in Periplasm Lysis buffer without protease inhibitors.
  Elute with 2 CV (5 ml) of 400 mM imidazole in Periplasm Lysis buffer without protease inhibitors.
  Load on Superdex HR 75 16/60 equilibrated and eluted in 1×PBS.
  Pool peak fractions and add 10% ultra-pure glycerol.
  Determine concentration according to the Molar Extinction Coefficient at 280 nm
  Freeze aliquots in liquid nitrogen and store at −80° C.

Method and Procedure for ELISA of B11 on Epha2
  Coat 96 well Nunc MaxiSorp Plate with 200 ng/well of recombinant hEphA2 in 100 µl 1×PBS.
  Incubate overnight at +4° C.
  1× wash in 1×PBS.
  Block with 200 µl/well of 3% BSA 1×PBS-0.05% Tween, 1 hr at room temperature.
  Add serial 1:2 dilutions of B11 from a concentration of 100 nM in 3% BSA 1×PBS-0.05% Tween and incubate 3 hrs at +4° C. with gently shaking.
  3 washes in 1×PBS-0.05% Tween+1 wash in 1×PBS.
  Add αFlag HRP diluted 1:1000 in 3% BSA 1×PBS-0.05% Tween and incubate for 1 hr at +4° C. as above.
  3 washes in 1×PBS-0.05% Tween+1 wash 1×PBS.
  Develop with 100 ul/well TMB and read OD370 nm with Multiskan Ascent instrument.

For ELISA Screening at 42° C. or in 4M Urea
  For ELISAs done at 42° C., plates are incubated at 42° C. prior to the study, reagents added per above method and plates placed back at 42° C. for various time points.
  For ELISAs done in 4M Urea, incubation is done at room temperature for 3 hrs with shaking and the 1×PBS/0.05% Tween/3% BSA solution is made to 4M Urea by adding Urea. All else is the same as above.

Method and Procedure to Measure Melting Temp of CH2
  Prepare a fresh dilution of Sypro Orange Protein Gel Stain from the 5000× stock (SIGMA Aldrich Cod S5692) to 4× in the Abdurin storage buffer (1×PBS, 10% glycerol).
  Place the appropriate reaction plate (Fast Optical 96-Well Reaction Plate) or tubes on ice, then prepare the protein melt reactions.
  Add reaction components to the plate in the order listed. Run the samples in triplicate.
    Abdurin at the final concentration of 0.2 mg/ml in storage buffer (15 µl);
    Diluted Sypro Orange dye (5 µl);
    Include a no-protein control with only buffer and dye as indicated above.
  Pipet each reaction up and down 10 times to mix well.
  Seal the plate with MicroAmp® Optical Adhesive Film, spin at 1000 rpm for 1 minute, then place on ice.
  Run at Real Time PCR Instrument according to the following Settings with the detector SYBR:
    For the reaction volume per well, enter 20 µl;
    For the ramp mode, select Continuous;
    Define the thermal profile:

| Step | Ramp rate | Temp (° C.) | Time (mm:ss) |
| --- | --- | --- | --- |
| 1 | 1.6° C./s | 25.0 | 02:00 |
| 2 | 0.05° C./s | 99.0 | 02:00 |

In a plot of fluorescence intensity vs. temperature, Tm values correspond to the inflection point of the transition curve and was calculated according to the Boltzmann method from each fluorescence profile.

What is claimed is:

1. An isolated modified CH2 domain molecule, comprising
a framework 1 region, a framework 2 region, a framework 3 region, a framework 4 region, a loop 1 located between the framework 1 region and the framework 2 region, a loop 2 located between the framework 2 region and the framework 3 region, and a loop 3 located between the framework 3 region and the framework 4 region,
wherein the modified CH2 domain molecule comprises at least one amino acid substitution in at least one of the framework 1 region, the framework 2 region, the framework 3 region, or the framework 4 region, as compared to a template CH2 domain molecule comprising the amino acid sequence of SEQ ID NO: 1 or SEQ ID NO: 12; and
wherein the at least one amino acid substitution is selected from the following: substitution of Val to Phe at position 27 (V27F) in the framework 1 region; substitution of Lys to Thr at position 84 (K84T) in the framework 3 region; or substitution of Ala to Asp at position 103 (A103D) in the framework 4 region.

2. The modified CH2 domain molecule of claim 1, wherein the at least one amino acid substitution comprises 1-3 amino acid substitutions in the framework 1 region.

3. The modified CH2 domain molecule of claim 2, wherein the at least one amino acid substitution comprises an amino acid substitution of Val to Phe at position 27 (V27F) in the framework 1 region.

4. The modified CH2 domain molecule of claim 1, wherein the at least one amino acid substitution comprises 1-3 amino acid substitutions in the framework 2 region.

5. The modified CH2 domain molecule of claim 1, wherein the at least one amino acid substitution comprises 1-3 amino acid substitutions in the framework 3 region.

6. The modified CH2 domain molecule of claim 5, wherein the at least one amino acid substitution comprises an amino acid substitution of Lys to Thr at position 84 (K84T) in the framework 3 region.

7. The modified CH2 domain molecule of claim 1, wherein the at least one amino acid substitution comprises 1-3 amino acid substitutions in the framework 4 region.

8. The modified CH2 domain molecule of claim 7, wherein the at least one amino acid substitution comprises an amino acid substitution of Ala to Asp at position 103 (A103D) in the framework 4 region.

9. The modified CH2 domain molecule of claim 1, wherein the at least one amino acid substitution comprises V27F, K84T and A103D.

10. The modified CH2 domain molecule of claim 9, wherein the at least one amino acid substitution further comprises an additional amino acid substitution selected from the group consisting of Leu to Met at position 15 (L15M) in the framework 1 region, Val to Ala at position 46((V46A) in the framework 2 region, Asn to His at position 50 (N50H) in the framework 2 region, Leu to Ser at position 73 (L73S) in the framework 3 region, and Glu to Gln at position 97 (E97Q) in the framework 4 region.

11. The modified CH2 domain molecule of claim 1, wherein
the framework 1 region consists of an amino acid sequence of GPSVFLFPPKPKDT(L,M)MISRTPE-VTCVFV (SEQ ID NO: 8),
the framework 2 region consists of an amino acid sequence of KFNWYVDG(V,A)EVH(N,H)AKTKPR (SEQ ID NO: 9),
the framework 3 region consists of an amino acid sequence of YRVVSVLTV(L,S)HQDWLNGKEYTCKV (SEQ ID NO: 10), and
the framework 4 region consists of an amino acid sequence of (E,Q)KTISKDK (SEQ ID NO: 11).

12. The modified CH2 domain molecule of claim 1, wherein the loop 1, loop 2 and loop 3 are identical with the loop 1, loop 2 and loop 3 of the template CH2 domain molecule of SEQ ID NO: 1.

13. The modified CH2 domain molecule of claim 1, wherein the loop 1, loop 2 and loop 3 are identical with the loop 1, loop 2 and loop 3 of the template CH2 domain molecule of SEQ ID NO: 12.

14. The modified CH2 domain molecule of claim 1, wherein the modified CH2 domain molecule binds FcRn (e.g., human FcRn).

15. The modified CH2 domain molecule of claim 1, wherein the modified CH2 domain molecule has a melting temperature (Tm) higher than 62° C.

16. The modified CH2 domain molecule of claim 1, wherein the modified CH2 domain molecule comprises at least one amino acid substitution, addition or deletion in one of loop 1, loop 2, or loop 3, as compared to a template CH2 domain molecule comprising the amino acid sequence of SEQ ID NO: 1 or SEQ ID NO: 12.

17. The modified CH2 domain molecule of claim 1, comprising an amino acid sequence selected from the group consisting of SEQ ID NOS: 3-7 and 22-26.

18. A library of modified CH2 domain molecules, wherein for each modified CH2 domain molecule in the library:
the framework 1 region consists of an amino acid sequence of GPSVFLFPPKPKDT(L,M)MISRTPE-VTCVFV (SEQ ID NO: 8),
the framework 2 region consists of an amino acid sequence of KFNWYVDG(V,A)EVH(N,H)AKTKPR (SEQ ID NO: 9),
the framework 3 region consists of an amino acid sequence of YRVVSVLTV(L,S)HQDWLNGKEYTCKV (SEQ ID NO: 10), and
the framework 4 region consists of an amino acid sequence of (E,Q)KTISKDK (SEQ ID NO: 11);
wherein the modified CH2 domain molecules in the library differ from one another in the loop 1, loop 2, and/or loop 3 region, and differ from a template CH2 domain molecule in the loop 1, loop 2, and/or loop 3 region, by at least one amino acid substitution, deletion, or addition.

19. The library of claim 18, wherein the template CH2 domain molecule is selected from the group consisting of SEQ ID NOS: 1, 2, and 12.

20. The library of claim 18, wherein the loop 3 region of each member in the library comprises the amino acid sequence of SNKALPAPI (SEQ ID NO: 15).

21. The library of claim 18, wherein the loop 1 region of each member in the library comprises an amino acid sequence selected from the group consisting of SEQ ID NO: 13, SEQ ID NO: 16 and SEQ ID NO: 18.

22. The library of claim 18, wherein the loop 2 region of each member in the library comprises an amino acid sequence selected from the group consisting of SEQ ID NO: 14, SEQ ID NO: 17 and SEQ ID NO: 19.

23. A method of identifying a CH2 domain molecule that binds to a target antigen, comprising
- contacting the target antigen with a library according to claim 18,
- identifying a CH2 domain molecule from the library that binds to the target antigen.

* * * * *

SEQUENCE LISTING

<160> NUMBER OF SEQ ID NOS: 26

<210> SEQ ID NO 1
<211> LENGTH: 104
<212> TYPE: PRT
<213> ORGANISM: Artificial Sequence
<220> FEATURE:
<223> OTHER INFORMATION: synthetic peptide - a template CH2 domain
      molecule (truncated human CH2)

<400> SEQUENCE: 1

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
                20                  25                  30

Glu Asp Pro Glu Val Lys Phe Asn Trp Tyr Val Asp Gly Val Glu Val
            35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 2
<211> LENGTH: 104
<212> TYPE: PRT
<213> ORGANISM: Artificial Sequence
<220> FEATURE:
<223> OTHER INFORMATION: synthetic peptide - a template CH2 domain
      molecule (truncated macaque CH2)

<400> SEQUENCE: 2

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser Gln
                20                  25                  30

Glu Asp Pro Asp Val Lys Phe Asn Trp Tyr Val Asn Gly Ala Glu Val
            35                  40                  45

His His Ala Gln Thr Lys Pro Arg Glu Thr Gln Tyr Asn Ser Thr Tyr
    50                  55                  60

Arg Val Val Ser Val Leu Thr Val Thr His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Gln Lys Thr Ile Ser Lys Asp Lys
            100

<210> SEQ ID NO 3
<211> LENGTH: 104
<212> TYPE: PRT
<213> ORGANISM: Artificial Sequence
<220> FEATURE:
<223> OTHER INFORMATION: synthetic peptide - ABD01

<400> SEQUENCE: 3

Gly Pro Ser Val Phe Leu Phe Pro Pro Lys Pro Lys Asp Thr Leu Met
1               5                   10                  15

```
Ile Ser Arg Thr Pro Glu Val Thr Cys Val Phe Val Asp Tyr Arg Ala
            20                  25                  30

Asp Tyr Leu Glu Val Lys Phe Asn Trp Tyr Val Asp Gly Val Glu Val
        35                  40                  45

His Asn Ala Lys Thr Lys Pro Arg Gln Tyr Asp Pro Leu Tyr Gly Tyr
    50                  55                  60

Arg Val Val Ser Val Leu Thr Val Leu His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Glu Lys Thr Ile Ser Lys Asp Lys
            100

<210> SEQ ID NO 4
<211> LENGTH: 104
<212> TYPE: PRT
<213> ORGANISM: Artificial Sequence
<220> FEATURE:
<223> OTHER INFORMATION: synthetic peptide - ABD02

<400> SEQUENCE: 4

Gly Pro Ser Val Phe Leu Phe Pro Pro Lys Pro Lys Asp Thr Leu Met
1               5                   10                  15

Ile Ser Arg Thr Pro Glu Val Thr Cys Val Phe Val Asp Tyr Arg Ala
            20                  25                  30

Asp Tyr Leu Glu Val Lys Phe Asn Trp Tyr Val Asp Gly Ala Glu Val
        35                  40                  45

His Asn Ala Lys Thr Lys Pro Arg Gln Tyr Asp Pro Leu Tyr Gly Tyr
    50                  55                  60

Arg Val Val Ser Val Leu Thr Val Leu His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Glu Lys Thr Ile Ser Lys Asp Lys
            100

<210> SEQ ID NO 5
<211> LENGTH: 104
<212> TYPE: PRT
<213> ORGANISM: Artificial Sequence
<220> FEATURE:
<223> OTHER INFORMATION: synthetic peptide - ABD03

<400> SEQUENCE: 5

Gly Pro Ser Val Phe Leu Phe Pro Pro Lys Pro Lys Asp Thr Leu Met
1               5                   10                  15

Ile Ser Arg Thr Pro Glu Val Thr Cys Val Phe Val Asp Tyr Arg Ala
            20                  25                  30

Asp Tyr Leu Glu Val Lys Phe Asn Trp Tyr Val Asp Gly Ala Glu Val
        35                  40                  45

His His Ala Lys Thr Lys Pro Arg Gln Tyr Asp Pro Leu Tyr Gly Tyr
    50                  55                  60

Arg Val Val Ser Val Leu Thr Val Ser His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Gln Lys Thr Ile Ser Lys Asp Lys
            100
```

<210> SEQ ID NO 6
<211> LENGTH: 104
<212> TYPE: PRT
<213> ORGANISM: Artificial Sequence
<220> FEATURE:
<223> OTHER INFORMATION: synthetic peptide - ABD04

<400> SEQUENCE: 6

Gly Pro Ser Val Phe Leu Phe Pro Pro Lys Pro Lys Asp Thr Met Met
1               5                   10                  15

Ile Ser Arg Thr Pro Glu Val Thr Cys Val Phe Val Asp Tyr Arg Ala
            20                  25                  30

Asp Tyr Leu Glu Val Lys Phe Asn Trp Tyr Val Asp Gly Ala Glu Val
        35                  40                  45

His His Ala Lys Thr Lys Pro Arg Gln Tyr Asp Pro Leu Tyr Gly Tyr
    50                  55                  60

Arg Val Val Ser Val Leu Thr Val Ser His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Glu Lys Thr Ile Ser Lys Asp Lys
            100

<210> SEQ ID NO 7
<211> LENGTH: 104
<212> TYPE: PRT
<213> ORGANISM: Artificial Sequence
<220> FEATURE:
<223> OTHER INFORMATION: synthetic peptide - ABD05

<400> SEQUENCE: 7

Gly Pro Ser Val Phe Leu Phe Pro Pro Lys Pro Lys Asp Thr Leu Met
1               5                   10                  15

Ile Ser Arg Thr Pro Glu Val Thr Cys Val Phe Val Asp Tyr Arg Ala
            20                  25                  30

Asp Tyr Leu Glu Val Lys Phe Asn Trp Tyr Val Asp Gly Ala Glu Val
        35                  40                  45

His His Ala Lys Thr Lys Pro Arg Gln Tyr Asp Pro Leu Tyr Gly Tyr
    50                  55                  60

Arg Val Val Ser Val Leu Thr Val Ser His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Glu Lys Thr Ile Ser Lys Asp Lys
            100

<210> SEQ ID NO 8
<211> LENGTH: 28
<212> TYPE: PRT
<213> ORGANISM: Artificial Sequence
<220> FEATURE:
<223> OTHER INFORMATION: synthetic peptide - the framework 1 region
<220> FEATURE:
<221> NAME/KEY: misc_feature
<222> LOCATION: (15)..(15)
<223> OTHER INFORMATION: Xaa is L or M

<400> SEQUENCE: 8

Gly Pro Ser Val Phe Leu Phe Pro Pro Lys Pro Lys Asp Thr Xaa Met
1               5                   10                  15

Ile Ser Arg Thr Pro Glu Val Thr Cys Val Phe Val
            20                  25

<210> SEQ ID NO 9
<211> LENGTH: 19
<212> TYPE: PRT
<213> ORGANISM: Artificial Sequence
<220> FEATURE:
<223> OTHER INFORMATION: synthetic peptide - the framework 2 region
<220> FEATURE:
<221> NAME/KEY: misc_feature
<222> LOCATION: (9)..(9)
<223> OTHER INFORMATION: Xaa is V or A
<220> FEATURE:
<221> NAME/KEY: misc_feature
<222> LOCATION: (13)..(13)
<223> OTHER INFORMATION: Xaa is N or H

<400> SEQUENCE: 9

Lys Phe Asn Trp Tyr Val Asp Gly Xaa Glu Val His Xaa Ala Lys Thr
1               5                   10                  15

Lys Pro Arg

<210> SEQ ID NO 10
<211> LENGTH: 24
<212> TYPE: PRT
<213> ORGANISM: Artificial Sequence
<220> FEATURE:
<223> OTHER INFORMATION: synthetic peptide - the framework 3 region
<220> FEATURE:
<221> NAME/KEY: misc_feature
<222> LOCATION: (10)..(10)
<223> OTHER INFORMATION: Xaa is L or S

<400> SEQUENCE: 10

Tyr Arg Val Val Ser Val Leu Thr Val Xaa His Gln Asp Trp Leu Asn
1               5                   10                  15

Gly Lys Glu Tyr Thr Cys Lys Val
            20

<210> SEQ ID NO 11
<211> LENGTH: 8
<212> TYPE: PRT
<213> ORGANISM: Artificial Sequence
<220> FEATURE:
<223> OTHER INFORMATION: synthetic peptide - the framework 4 region
<220> FEATURE:
<221> NAME/KEY: misc_feature
<222> LOCATION: (1)..(1)
<223> OTHER INFORMATION: Xaa is E or Q

<400> SEQUENCE: 11

Xaa Lys Thr Ile Ser Lys Asp Lys
1               5

<210> SEQ ID NO 12
<211> LENGTH: 104
<212> TYPE: PRT
<213> ORGANISM: Artificial Sequence
<220> FEATURE:
<223> OTHER INFORMATION: synthetic peptide - B11

<400> SEQUENCE: 12

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Tyr Arg Ala
            20                  25                  30

```
Asp Tyr Leu Glu Val Lys Phe Asn Trp Tyr Val Asp Gly Val Glu Val
            35                  40                  45

His Asn Ala Lys Thr Lys Pro Arg Gln Tyr Asp Pro Leu Tyr Gly Tyr
        50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 13
<211> LENGTH: 9
<212> TYPE: PRT
<213> ORGANISM: Artificial Sequence
<220> FEATURE:
<223> OTHER INFORMATION: synthetic peptide - human CH2 loop 1

<400> SEQUENCE: 13

Asp Val Ser His Glu Asp Pro Glu Val
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic peptide - human CH2 loop 2

<400> SEQUENCE: 14

Glu Glu Gln Tyr Asn Ser Thr
1               5

<210> SEQ ID NO 15
<211> LENGTH: 9
<212> TYPE: PRT
<213> ORGANISM: Artificial Sequence
<220> FEATURE:
<223> OTHER INFORMATION: synthetic peptide - human or macaque or B11
      loop 3

<400> SEQUENCE: 15

Ser Asn Lys Ala Leu Pro Ala Pro Ile
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic peptide - macaque CH2 loop 1

<400> SEQUENCE: 16

Asp Val Ser Gln Glu Asp Pro Asp Val
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic peptide - macaque CH2 loop 2

<400> SEQUENCE: 17
```

```
Glu Thr Gln Tyr Asn Ser Thr
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic peptide - B11 loop 1

<400> SEQUENCE: 18

Asp Tyr Arg Ala Asp Tyr Leu Glu Val
1               5

<210> SEQ ID NO 19
<211> LENGTH: 7
<212> TYPE: PRT
<213> ORGANISM: Artificial Sequence
<220> FEATURE:
<223> OTHER INFORMATION: synthetic peptide - B11 loop 2

<400> SEQUENCE: 19

Gln Tyr Asp Pro Leu Tyr Gly
1               5

<210> SEQ ID NO 20
<211> LENGTH: 110
<212> TYPE: PRT
<213> ORGANISM: Artificial Sequence
<220> FEATURE:
<223> OTHER INFORMATION: synthetic peptide - wild type human CH2 domain

<400> SEQUENCE: 20

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 21
<211> LENGTH: 110
<212> TYPE: PRT
<213> ORGANISM: Artificial Sequence
<220> FEATURE:
<223> OTHER INFORMATION: synthetic peptide - macaque CH2 domain

<400> SEQUENCE: 21

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser Gln Glu Asp Pro Asp Val Lys Phe Asn Trp Tyr
            35                  40                  45
```

Val Asn Gly Ala Glu Val His His Ala Gln Thr Lys Pro Arg Glu Thr
 50                  55                  60

Gln Tyr Asn Ser Thr Tyr Arg Val Val Ser Val Leu Thr Val Thr His
 65                  70                  75                  80

Gln Asp Trp Leu Asn Gly Lys Glu Tyr Thr Cys Lys Val Ser Asn Lys
                 85                  90                  95

Ala Leu Pro Ala Pro Ile Gln Lys Thr Ile Ser Lys Asp Lys
            100                 105                 110

<210> SEQ ID NO 22
<211> LENGTH: 104
<212> TYPE: PRT
<213> ORGANISM: Artificial Sequence
<220> FEATURE:
<223> OTHER INFORMATION: synthetic peptide - ABD06

<400> SEQUENCE: 22

Gly Pro Ser Val Phe Leu Phe Pro Pro Lys Pro Lys Asp Thr Leu Met
 1               5                  10                  15

Ile Ser Arg Thr Pro Glu Val Thr Cys Val Phe Val Asp Val Ser His
                 20                  25                  30

Glu Asp Pro Glu Val Lys Phe Asn Trp Tyr Val Asp Gly Val Glu Val
             35                  40                  45

His Asn Ala Lys Thr Lys Pro Arg Glu Glu Gln Tyr Asn Ser Thr Tyr
 50                  55                  60

Arg Val Val Ser Val Leu Thr Val Leu His Gln Asp Trp Leu Asn Gly
 65                  70                  75                  80

Lys Glu Tyr Thr Cys Lys Val Ser Asn Lys Ala Leu Pro Ala Pro Ile
                 85                  90                  95

Glu Lys Thr Ile Ser Lys Asp Lys
            100

<210> SEQ ID NO 23
<211> LENGTH: 104
<212> TYPE: PRT
<213> ORGANISM: Artificial Sequence
<220> FEATURE:
<223> OTHER INFORMATION: synthetic peptide - ABD07

<400> SEQUENCE: 23

Gly Pro Ser Val Phe Leu Phe Pro Pro Lys Pro Lys Asp Thr Leu Met
 1               5                  10                  15

Ile Ser Arg Thr Pro Glu Val Thr Cys Val Phe Val Asp Val Ser His
                 20                  25                  30

Glu Asp Pro Glu Val Lys Phe Asn Trp Tyr Val Asp Gly Ala Glu Val
             35                  40                  45

His Asn Ala Lys Thr Lys Pro Arg Glu Glu Gln Tyr Asn Ser Thr Tyr
 50                  55                  60

Arg Val Val Ser Val Leu Thr Val Leu His Gln Asp Trp Leu Asn Gly
 65                  70                  75                  80

Lys Glu Tyr Thr Cys Lys Val Ser Asn Lys Ala Leu Pro Ala Pro Ile
                 85                  90                  95

Glu Lys Thr Ile Ser Lys Asp Lys
            100

<210> SEQ ID NO 24
<211> LENGTH: 104
<212> TYPE: PRT
<213> ORGANISM: Artificial Sequence
<220> FEATURE:
<223> OTHER INFORMATION: synthetic peptide - ABD08

<400> SEQUENCE: 24

Gly Pro Ser Val Phe Leu Phe Pro Pro Lys Pro Lys Asp Thr Leu Met
1               5                   10                  15

Ile Ser Arg Thr Pro Glu Val Thr Cys Val Phe Val Asp Val Ser His
            20                  25                  30

Glu Asp Pro Glu Val Lys Phe Asn Trp Tyr Val Asp Gly Ala Glu Val
        35                  40                  45

His His Ala Lys Thr Lys Pro Arg Glu Glu Gln Tyr Asn Ser Thr Tyr
    50                  55                  60

Arg Val Val Ser Val Leu Thr Val Ser His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Gln Lys Thr Ile Ser Lys Asp Lys
            100

<210> SEQ ID NO 25
<211> LENGTH: 104
<212> TYPE: PRT
<213> ORGANISM: Artificial Sequence
<220> FEATURE:
<223> OTHER INFORMATION: synthetic peptide - ABD09

<400> SEQUENCE: 25

Gly Pro Ser Val Phe Leu Phe Pro Pro Lys Pro Lys Asp Thr Met Met
1               5                   10                  15

Ile Ser Arg Thr Pro Glu Val Thr Cys Val Phe Val Asp Val Ser His
            20                  25                  30

Glu Asp Pro Glu Val Lys Phe Asn Trp Tyr Val Asp Gly Ala Glu Val
        35                  40                  45

His His Ala Lys Thr Lys Pro Arg Glu Glu Gln Tyr Asn Ser Thr Tyr
    50                  55                  60

Arg Val Val Ser Val Leu Thr Val Ser His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Glu Lys Thr Ile Ser Lys Asp Lys
            100

<210> SEQ ID NO 26
<211> LENGTH: 104
<212> TYPE: PRT
<213> ORGANISM: Artificial Sequence
<220> FEATURE:
<223> OTHER INFORMATION: synthetic peptide - ABD10

<400> SEQUENCE: 26

Gly Pro Ser Val Phe Leu Phe Pro Pro Lys Pro Lys Asp Thr Leu Met
1               5                   10                  15

Ile Ser Arg Thr Pro Glu Val Thr Cys Val Phe Val Asp Val Ser His
            20                  25                  30

Glu Asp Pro Glu Val Lys Phe Asn Trp Tyr Val Asp Gly Ala Glu Val
        35                  40                  45

His His Ala Lys Thr Lys Pro Arg Glu Glu Gln Tyr Asn Ser Thr Tyr
    50                  55                  60

-continued

```
Arg Val Val Ser Val Leu Thr Val Ser His Gln Asp Trp Leu Asn Gly
65              70                  75                  80

Lys Glu Tyr Thr Cys Lys Val Ser Asn Lys Ala Leu Pro Ala Pro Ile
                85                  90                  95

Glu Lys Thr Ile Ser Lys Asp Lys
                100
```